United States Patent
Lee et al.

(10) Patent No.: US 8,908,955 B2
(45) Date of Patent: Dec. 9, 2014

(54) METHOD AND SYSTEM FOR PROVIDING STEREOSCOPIC X-RAY IMAGE

(75) Inventors: Kang-eui Lee, Yongin-si (KR);
Myung-jin Chung, Seoul (KR);
Young-hun Sung, Hwaseong-si (KR);
Jong-ha Lee, Hwaseong-si (KR);
Kwang-eun Jang, Busan (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 196 days.

(21) Appl. No.: 13/482,972

(22) Filed: May 29, 2012

(65) Prior Publication Data
US 2012/0321167 A1 Dec. 20, 2012

(30) Foreign Application Priority Data
Jun. 15, 2011 (KR) .......................... 10-2011-0057971

(51) Int. Cl.
*G06K 9/00* (2006.01)
*A61B 6/02* (2006.01)
*G06T 11/00* (2006.01)
*A61B 6/00* (2006.01)
*H04N 13/02* (2006.01)

(52) U.S. Cl.
CPC .............. *A61B 6/022* (2013.01); *G06T 11/006* (2013.01); *A61B 6/486* (2013.01); *G06T 2211/436* (2013.01); *H04N 13/0221* (2013.01)
USPC ........................................... 382/132; 378/41

(58) Field of Classification Search
USPC .............. 382/132, 131, 128, 100; 378/41
See application file for complete search history.

(56) References Cited

U.S. PATENT DOCUMENTS

| | | | |
|---|---|---|---|
| 6,381,302 B1 * | 4/2002 | Berestov .................. 378/41 |
| 7,245,694 B2 * | 7/2007 | Jing et al. ................ 378/37 |
| 7,356,113 B2 * | 4/2008 | Wu et al. ................. 378/27 |
| 7,379,582 B2 * | 5/2008 | Katayama et al. ....... 382/154 |
| 8,452,379 B2 * | 5/2013 | DeFreitas et al. ....... 600/427 |
| 8,611,492 B2 * | 12/2013 | Jerebko .................. 378/37 |
| 2006/0291618 A1 * | 12/2006 | Eberhard et al. ......... 378/23 |
| 2007/0263765 A1 * | 11/2007 | Wu ........................ 378/37 |
| 2011/0058724 A1 * | 3/2011 | Claus .................... 382/132 |

FOREIGN PATENT DOCUMENTS

| | | |
|---|---|---|
| JP | 2005-136726 | 5/2005 |
| JP | 2005-168601 | 6/2005 |
| JP | 2007-229201 | 9/2007 |
| JP | 2010-187735 | 9/2010 |
| WO | WO 2008/043020 A2 | 4/2008 |

\* cited by examiner

Primary Examiner — Yon Couso
(74) Attorney, Agent, or Firm — NSIP Law (57) ABSTRACT

A method of providing a stereoscopic X-ray image is provided. The method includes acquiring X-ray images captured at respective rotation angles with respect to a part of a patient to be examined while rotating around the part to be examined, and in response to information regarding a viewpoint with respect to the part to be examined being input, using X-ray images at respective rotation angles corresponding to the viewpoint from among the acquired X-ray images to generate a three-dimensional (3D) X-ray image.

19 Claims, 5 Drawing Sheets

METHOD AND SYSTEM FOR PROVIDING STEREOSCOPIC X-RAY IMAGE

CROSS-REFERENCE TO RELATED APPLICATIONS

This application claims the benefit of Korean Patent Application No. 10-2011-0057971, filed on Jun. 15, 2011, in the Korean Intellectual Property Office, the entire disclosure of which is incorporated herein by reference for all purposes.

BACKGROUND

1. Field

The following description relates to a method and an apparatus for providing a stereoscopic X-ray image.

2. Description of the Related Art

X-ray technology is used in medical field, industrial field, scientific field, etc. In the medical field, X-ray technology may be utilized in diagnosing the health of a patient. X-ray technology may be used to visualize an anatomical structure of a human body. Thus, the X-ray technology may be used to perceive a pathological phenomenon, a disease, or an abnormal anatomical structure inside the human body. As another aspect, X-ray technology has difficulty in providing three-dimensional (3D) information about an internal structure of a human body. In other words, because X-ray images may exist as films or 2D images using an image sensor, a 3D effect or a sense of reality is decreased in response to the inside of a human body being examined in the medical field. Thus, research is being conducted into extracting 3D information from the inside of a human body of a patient while limiting the patient's exposure to radiation.

SUMMARY

According to an aspect, a method of providing a stereoscopic X-ray image is provided. The method includes acquiring X-ray images captured at respective rotation angles with respect to a part of a patient to be examined while rotating around the part to be examined, and in response to information regarding a viewpoint with respect to the part to be examined being input, using X-ray images at respective rotation angles corresponding to the viewpoint from among the acquired X-ray images to generate a three-dimensional (3D) X-ray image.

The generating may include, in response to the viewpoint being changed, using X-ray images at rotation angles corresponding to the changed viewpoint to generate a 3D X-ray image.

The generating may include generating the 3D X-ray image based on binocular disparity, and the X-ray images corresponding to the viewpoint may be at least one pair of X-ray images respectively corresponding to both eyes of a user from among the acquired X-ray images.

The X-ray images captured at the respective rotation angles may be captured under a same X-ray dose condition.

The X-ray dose condition may be changed via a user input.

The viewpoint may indicate information regarding a direction desired by a user to view with respect to the part to be examined.

The generating may include storing the acquired X-ray images, and in response to the information regarding a viewpoint being input by a user, reading X-ray images corresponding to the viewpoint from among the stored X-ray images and processing the read X-ray images as a 3D X-ray image.

The method may include receiving the information regarding a viewpoint, an X-ray dose condition with respect to the part to be examined, or any combination thereof.

The acquiring may include acquiring the X-ray images by using at least one X-ray generator.

The acquiring may include, in response to two or more X-ray generators being used, using the X-ray generators to acquire at least one pair of X-ray images at the same time.

The acquiring of the X-ray images may be in two-dimensions (2D).

The method may include displaying the generated 3D X-ray images.

A computer-readable recording medium may store a computer-readable program for executing the method in a computer.

In another aspect, a system for providing a stereoscopic X-ray image is provided. The system includes an image acquisition apparatus configured to acquire X-ray images captured at respective rotation angles with respect to a part of a patient to be examined while rotating around the part to be examined, and an image generation apparatus configured to, in response to information regarding a viewpoint with respect to the part to be examined being input, using X-ray images at respective rotation angles corresponding to the viewpoint from among the acquired X-ray images to generate a three-dimensional (3D) X-ray image.

In response to the viewpoint being changed, the image generation apparatus may use X-ray images at rotation angles corresponding to the changed viewpoint to generate a 3D X-ray image.

The image generation apparatus may generate the 3D X-ray image based on binocular disparity, and the X-ray images corresponding to the viewpoint may be at least one pair of X-ray images respectively corresponding to both eyes of a user from among the acquired X-ray images.

The X-ray images captured at the respective rotation angles may be captured under a same X-ray dose condition.

The X-ray dose condition may be changed via a user input.

The viewpoint may indicate information regarding a direction desired by a user to view with respect to the part to be examined.

The image generation apparatus may include an image storage unit configured to store the acquired X-ray images, and a 3D image processing unit configured to, in response to the information regarding a viewpoint being input by a user, read X-ray images corresponding to the viewpoint from among the stored X-ray images and process the read X-ray images as a 3D X-ray image.

The system may include an input apparatus configured to receive the information regarding a viewpoint, an X-ray dose condition with respect to the part to be examined, or any combination thereof.

The image acquisition apparatus may use at least one X-ray generator to acquire the X-ray images, and in response to two or more X-ray generators being used, the image acquisition apparatus may use the X-ray generators to acquire at least one pair of X-ray images at the same time.

In another aspect, an imaging device for providing a stereoscopic X-ray image is provided. The imaging device includes an imaging unit, the imaging unit including an image acquisition apparatus configured to acquire X-ray images captured at respective rotation angles with respect to a part of a patient to be examined while rotating around the part to be examined, and an image generation apparatus configured to use X-ray images at respective rotation angles corresponding to a viewpoint from among the acquired X-ray images to generate a three-dimensional (3D) X-ray image. Other fea-

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Figure 1:
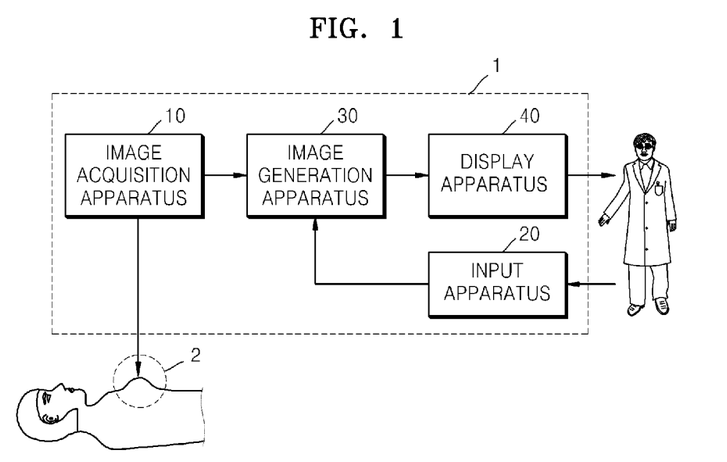
FIG. 1 is a diagram illustrating an example of a stereoscopic X-ray image providing system.

FIG. 1 illustrates a stereoscopic X-ray image providing system 1. Referring to FIG. 1, the stereoscopic X-ray image providing system 1 includes an image acquisition apparatus 10, an input apparatus 20, an image generation apparatus 30, and a display apparatus 40.

For the stereoscopic X-ray image providing system 1, only components associated with the current example are shown in FIG. 1. It is understood by one of ordinary skill in the art that general-use components may be included in the stereoscopic X-ray image providing system 1. Thus, descriptions of the general-use components are omitted for conciseness.

The stereoscopic X-ray image providing system 1 provides a three-dimensional (3D) X-ray image with respect to a part 2 to be examined of a patient. In the current example, the part 2 to be examined of the patient is assumed to be a breast region of the patient. Although the stereoscopic X-ray image providing system 1 may be a mammography system, it is understood by one of ordinary skill in the art that the stereoscopic X-ray image providing system 1 may be a system for providing a medical 3D X-ray image for another body part of the patient instead of the breast region.

An X-ray is an electromagnetic wave having a shorter wavelength than visible light. The X-ray may be generated by colliding an electron ray emitted at a high speed from a cathode to a heavy metal. The collision discharges electrons in a vacuum state, has a very strong transmittance with respect to a physical solid and has a fluorescent effect. Thus, in response to the X-ray being radiated onto the part 2 to be examined, some of the X-ray is absorbed by the part 2 to be examined. Therefore, the X-ray may be attenuated to ascertain a variation of density or thickness of the inside of the part 2 to be examined. The image acquisition apparatus 10 uses this X-ray characteristic to acquire a 2D X-ray image relating to a shape and structure of the inside of the part 2 to be examined.

The image acquisition apparatus 10 may acquire X-ray images captured at respective rotation angles with respect to the part 2 to be examined while rotating around the part 2 to be examined of the patient. The image acquisition apparatus 10 may include at least one X-ray generator to acquire the X-ray images.

In this example, the X-ray images captured at the respective rotation angles may be captured under the same X-ray dose. X-ray transmittance for transmitting the X-ray through the part 2 to be examined may vary according to X-ray dose. The X-ray dose may correspond with the intensity of the X-ray. Thus, a user may use the input apparatus 20 before the capturing starts to input a dose condition for capturing an image. The user's input in the input apparatus 20 before the image capturing starts may change the dose condition. As described above, in response to the image acquisition apparatus 10 radiating X-ray beams to the part 2 to be examined according to various dose conditions, the image acquisition apparatus 10 may acquire X-ray images with different transmittances.

The operation of the image acquisition apparatus 10 will be further described with reference to FIGS. 2A and 2B. Although the image acquisition apparatus 10 may include an X-ray generator and an X-ray detector in the current example, the X-ray generator and the X-ray detector are not shown in FIG. 1. As another aspect, because a general description of internal structures of general components, such as the X-ray generator for radiating an X-ray beam and the X-ray detector for detecting a transmitted X-ray beam, in the image acquisition apparatus 10, is well-known to those of ordinary skill in the art, the general description of the internal structures of the general components is omitted herein for conciseness.

Figure 2A:
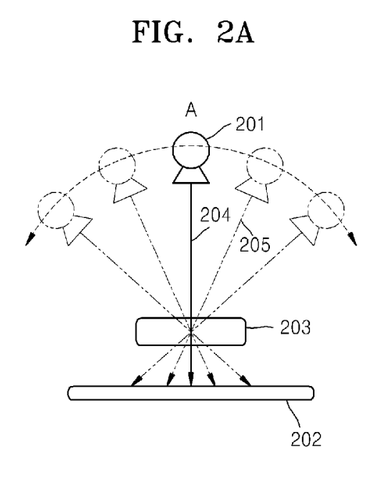
FIG. 2A illustrates an operation of an example of an image acquisition apparatus.

FIG. 2A illustrates an example of an operation of the image acquisition apparatus 10. Referring to FIG. 2A, unlike the example illustrated in FIG. 2B to be described below, the image acquisition apparatus 10 may include a single X-ray generator A 201.

The X-ray generator A 201 may radiate an X-ray beam while rotating around a part 203 of a patient. The part 203 is to be examined. An X-ray detector 202 may detect X-ray beams transmitted during the rotation and acquire X-ray images based on detection results. The X-ray detector 202 processes each of the X-ray images acquired based on the detection results as a 2D X-ray image by a 2D image processing unit 3210 shown in FIG. 3.

As another aspect, the X-ray generator A 201 may radiate X-ray beams to the part 203 to be examined at respective rotation angles while the X-ray generator A 201 rotates about the part 203 to be examined. For example, the X-ray generator A 201 may stop at a predetermined rotation angle 204 to radiate an X-ray beam and stop at another predetermined rotation angle 205 to radiate an X-ray beam. These predetermined rotation angles 204 and 205 may be arbitrarily set and changed by the user based on a use environment.

The X-ray detector 202 may detect the radiated X-ray beams and acquire an X-ray image based on each of the detected X-ray beams. At this time, the X-ray detector 202 may map, to the acquired X-ray image, information relating to rotation angle that the acquired X-ray image is acquired at.

Figure 2B:
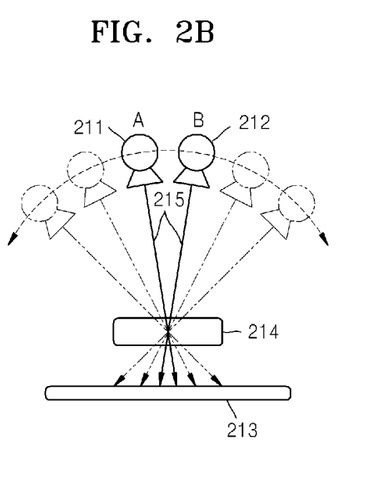
FIG. 2B illustrates another example of an operation of the image acquisition apparatus.

FIG. 2B illustrates another example of an operation of the image acquisition apparatus 10. Referring to FIG. 2B, unlike the example illustrated in FIG. 2A described above, the image acquisition apparatus 10 may include two X-ray generators A 211 and B 212. Although a distance between the X-ray generator A 211 and the X-ray generator B 212 may correspond to binocular disparity of a human being, the current example is not limited to the distance. Also, the number of X-ray generators in the current example is not limited to 2 and may be more than 2. In other words, only the two X-ray generators A 211 and B 212 are shown in the current example for conciseness.

The X-ray generator A 211 and the X-ray generator B 212 may radiate X-ray beams to a part 214 to be examined of a patient while rotating around the part 214 to be examined. Unlike the example illustrated in FIG. 2A, the X-ray generator A 211 and the X-ray generator B 212 may radiate a pair of X-ray beams at substantially the same time. An X-ray detector 213 may detect transmitted X-ray beams during the rotation and acquire a pair of X-ray images at the same time based on detected results. Thus, in response to the image acquisition apparatus 10 including two or more X-ray generators, the image acquisition apparatus 10 may acquire at least one pair of X-ray images at substantially the same time.

As another aspect, the pair of X-ray generators A 211 and B 212 may rotate together about the part 214 to be examined and radiate respective X-ray beams to the part 214 to be examined at respective rotation angles. As an example, the X-ray generator A 211 may radiate an X-ray beam at a predetermined rotation angle 215 at substantially the same time as the X-ray generator B 212 radiates an X-ray beam at the predetermined rotation angle 215. Thereafter, the pair of X-ray generators A 211 and B 212 may radiate X-ray beams at another rotation angle in substantially the same manner.

The X-ray detector 213 may detect the X-ray beams radiated by the X-ray generators A 211 and B 212 and acquire X-ray images based on the detected X-ray beams. At this time, the X-ray detector 213 may map, to the acquired X-ray image, information relating to a rotation angle of each of the acquired X-ray images is acquired at.

According to the examples of FIGS. 2A and 2B, the image acquisition apparatus 10 may acquire X-ray images of the part 2 to be examined at various rotation angles. Although the acquired X-ray images may correspond to 2D images, the acquired X-ray images may be used to generate a 3D X-ray image by the image generation apparatus 30 of FIG. 1.

Referring back to FIG. 1, the image generation apparatus 30 may generates a 3D X-ray image. As another aspect, in response to information regarding a viewpoint relating to the part 2 to be examined being input, the image generation apparatus 30 may use X-ray images of rotation angles corresponding to the viewpoint from among the acquired X-ray images to generate a 3D X-ray image. In the examples, the viewpoint includes information about a direction in which the user desires to view the part 2 to be examined. The user may be a doctor, an examiner, or the like.

The input apparatus 20 may receive from the user information relating to a viewpoint. The viewpoint may indicate a direction in which the user desires to view the part 2 to be examined. As described above, the input apparatus 20 may receive an X-ray dose condition for capturing. The image generation apparatus 30 generates a 3D X-ray image relating to the viewpoint, the dose input through the input apparatus 20, or any combination thereof. The input apparatus 20 may include any generally known information input tools, such as a keyboard, a mouse, a touch screen, voice recognition, and the like.

Figure 3:
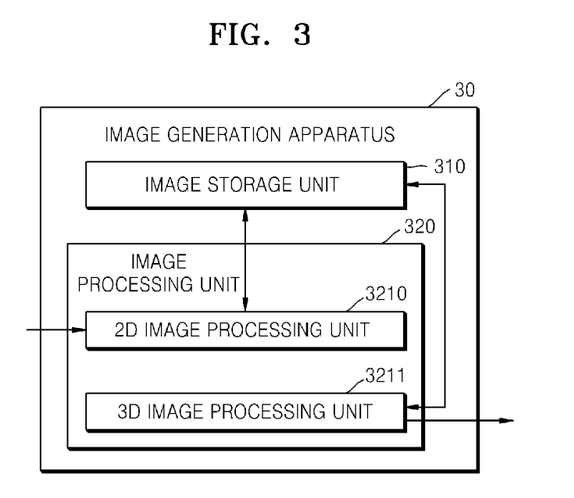
FIG. 3 is a diagram illustrating an example of an image generation apparatus.

FIG. 3 illustrates an example of the image generation apparatus 30. Referring to FIG. 3, the image generation apparatus 30 includes an image storage unit 310 and an image processing unit 320. The image processing unit 320 may include a 2D image processing unit 3210 and a 3D image processing unit 3211.

The image processing unit 320 may be implemented as one or a plurality of processors. The processor may be implemented by an array of a plurality of logic gates or a combination of a general-use microprocessor and a memory for storing a program executable in the general-use microprocessor. In addition, one of ordinary skill in the art understands that the processor may be implemented by other types of hardware.

The 2D image processing unit 3210 may process the X-ray images acquired by the image acquisition apparatus 10 to generate 2D X-ray images. The 2D image processing unit 3210 may transmit the generated 2D X-ray images to the image storage unit 310. Since processing images in the 2D image processing unit 3210 may be a simple 2D X-ray image processing process understood by one of ordinary skill in the art, a detailed description thereof will be omitted for conciseness.

The image storage unit 310 may store all of the generated 2D X-ray images. In other words, the image storage unit 310 may store all of the X-ray images acquired by the image acquisition apparatus 10 before the 3D image processing unit 3211 generates a 3D X-ray image. After the X-ray images are stored, the image storage unit 310 may transmit only X-ray images required for the 3D image processing unit 3211 to the 3D image processing unit 3211.

The image generation apparatus 30 may generate a 3D X-ray image based on binocular disparity. In another aspect, the 3D image processing unit 3211 may be in charge of a process of generating a 3D X-ray image.

In response to information regarding a viewpoint being input from the user, the 3D image processing unit 3211 may read X-ray images corresponding to the input viewpoint from among the stored X-ray images and process the read X-ray images as the 3D X-ray image to generate a 3D X-ray image. In this example, the X-ray images corresponding to the input viewpoint may correspond to at least one pair of X-ray images corresponding to both eyes of the user from among the acquired X-ray images.

The principle of processing a 3D X-ray image in the 3D image processing unit 3211 according to the current example is described below.

Since both eyes of a human being are spaced apart from each other by about 65 mm, binocular disparity exists. The binocular disparity may cause a 3D effect. As another aspect, both eyes view 2D images that are a little bit different from each other, respectively, and the two images are transferred to the brain via the retina of each eye. The brain senses perspective and presence of a 3D image to the two images by correctly synthesizing the two images, causing the human being to perceive the 3D effect. This perception is called stereoscopy.

For example, in response to a 3D stereoscopic movie being filmed, every movie scene is simultaneously captured from the perspective of the left and right eyes with two movie cameras. This capturing process is similar to a human being viewing an object with both eyes. The scenes of the two films captured from the perspective of the left and right eyes are each a little different. While the two films are being simultaneously projected, the scenes of the two films are respectively perceived by both eyes, and therefore the brain senses a 3D effect.

There are various methods of recognizing two different scenes by both eyes while the two different scenes are being simultaneously projected onto a single screen to allow a human being to feel a 3D effect. Examples of the methods include a polarizing filter using method, an anaglyph method, and the like. The polarizing filter using method is described below, as a representative example.

In a case of a 3D stereoscopic movie that uses a polarizing filter, two images are passed through polarizing filters. The polarizing filters are oriented in different directions, and the two polarized images are projected onto a screen. Moviegoers may enjoy the 3D stereoscopic movie only if they wear glasses with polarizing filters. In this example, polarizing directions of the polarizing filters used in the right lens and the left lens of the glasses may cross each other by 90°. Since the polarizing filters do not pass light polarized in non-defined directions, each moviegoer views the different images with their right eye and their left eye causing the brain to three-dimensionally perceive the projected images.

Methods of implementing a 3D stereoscopic movie without using glasses also exist, such as a lenticular lens method, a parallax barrier method, an integrated imaging method, a volume imaging method, a hologram method, and the like. Since the methods of implementing a 3D stereoscopic movie are only used to aid in the understanding of the current example and are well known to one of ordinary skill in the art, detailed descriptions thereof will be omitted for conciseness.

The 3D image processing unit 3211 may use the above-described methods of implementing a 3D stereoscopic movie based on binocular disparity.

As another aspect, because the X-ray images stored in the image storage unit 310 may be captured and acquired while the image acquisition apparatus 10 may be rotated around the part 2 to be examined, at least one pair of X-ray images from among the stored X-ray images may correspond to binocular disparity. For example, in response to an assumption that the binocular disparity is 65 mm, a pair of X-ray images acquired at angles where a distance between positions of the X-ray generator A 201 is 65 mm from among the stored X-ray images may correspond to the left and right eyes.

Thus, the 3D image processing unit 3211 may read at least one pair of X-ray images corresponding to both eyes from the image storage unit 310 to generate a 3D X-ray image.

In this case, the 3D image processing unit 3211 may consider information relating to a viewpoint that is input via the input apparatus by the user with respect to which types of X-ray images are read. As described above, a viewpoint relates to information corresponding to a direction in which the user desires to view a part to be examined.

The 3D image processing unit 3211 reads X-ray images of rotation angles corresponding to the viewpoint. In other words, the 3D image processing unit 3211 considers angles at which a distance between positions of the X-ray generator A 201 is 65 mm based on a direction indicated by the viewpoint to read X-ray images and generates a 3D X-ray image from the read X-ray images. As described above, in response to information regarding a viewpoint being input by the user, the 3D image processing unit 3211 reads X-ray images corresponding to the viewpoint, for example, at least one pair of X-ray images corresponding to both eyes, from among the stored X-ray images to generate a 3D X-ray image.

Since a method of synthesizing the at least one pair of read X-ray images corresponding to the both eyes in the 3D image processing unit 3211 is similar to the above-described method of synthesizing a 3D stereoscopic movie and the method of synthesizing the at least one pair of read X-ray images is well known to one of ordinary skill in the art, a detailed description of the method of synthesizing the at least one pair of read X-ray images will be omitted for conciseness.

The 3D image processing unit 3211 generates a 3D X-ray image based on the above-described method.

Referring back to FIG. 1, because the image acquisition apparatus 10 may acquire X-ray images at different rotation angles as described above, the 3D image processing unit 3211 may generate 3D X-ray images in various directions with respect to the part 2 to be examined.

In response to a new viewpoint being input by the user, the image generation apparatus 30 may use X-ray images at rotation angles corresponding to the new viewpoint to generate a 3D X-ray image. In other words, in response to the user changing a viewpoint of the part 2 to be examined via the input apparatus 20, the image generation apparatus 30 may generate a 3D X-ray image based on the changed viewpoint.

The display apparatus 40 may display the generated 3D X-ray image. As described above, the display apparatus 40 may display the generated 3D X-ray image by passing the generated 3D X-ray image through polarizing filters of different directions, and the display apparatus 40 may correspond to a kind of monitor. However, one of ordinary skill in the art understands that the display apparatus 40 may include generally known apparatuses for displaying a 3D image.

Figure 4:
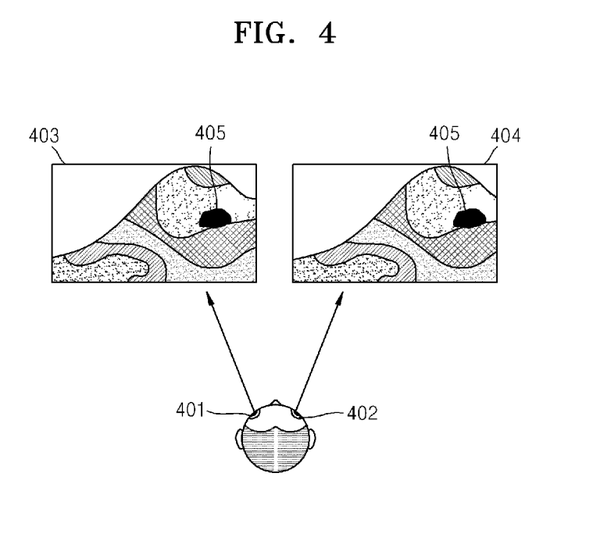
FIG. 4 illustrates examples of X-ray images of a part to be examined that correspond to both eyes.

FIG. 4 illustrates examples of X-ray images 403 and 404 of a part to be examined that correspond to both eyes 401 and 402. Referring to FIG. 4, the X-ray image 403 corresponding to the left eye 401 and the X-ray image 404 corresponding to the right eye 402 may be shown. The X-ray images 403 and 404 may be associated with a breast tissue that includes a tumor 405.

The 3D image processing unit 3211 may read the X-ray images 403 and 404 at rotation angles corresponding to a viewpoint input by the user from among the X-ray images stored in the image storage unit 310. Since the X-ray images 403 and 404 may be acquired at different rotation angles, a difference between the X-ray images 403 and 404 may exist. As another aspect, because the X-ray images 403 and 404 may be acquired under the same dose condition, depths of the X-ray images 403 and 404 may be the same.

Figure 5A:
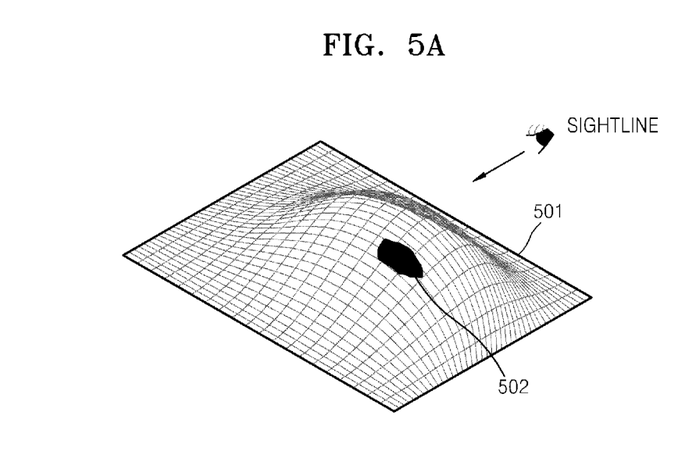
FIG. 5A illustrates an example of a 3D X-ray image generated by the image generation apparatus.

FIG. 5A illustrates an example of a 3D X-ray image 501 generated by the image generation apparatus 30. Referring to FIG. 5A, the 3D X-ray image 501 displayed on the display apparatus 40 is viewed by the user through glasses with polarizing filters. The user may feel a 3D effect of the 3D X-ray image 501 due to binocular disparity and may perceive information regarding a position, size, and depth of a tumor 502 hidden by overlapped tissues.

Figure 5B:
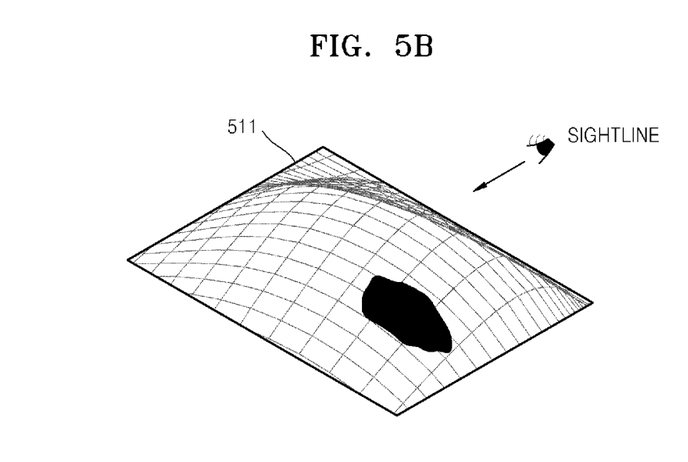
FIG. 5B illustrates an example of a 3D X-ray image corresponding to another viewpoint different from that of FIG. 5A.

FIG. 5B illustrates an example of a 3D X-ray image 511 corresponding to another viewpoint different from that of FIG. 5A. Referring to FIG. 5B, the 3D X-ray image 511 is an image of a case where a viewpoint towards a part to be examined is changed when compared with the 3D X-ray image 501 of FIG. 5A. Since the viewpoint is changed, the viewpoint of the 3D X-ray image 521 is different from the viewpoint of the 3D X-ray image 501 of FIG. 5A.

Figure 5C:
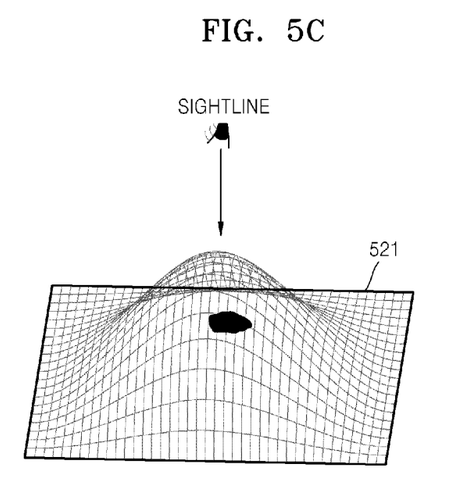
FIG. 5C illustrates an example of a 3D X-ray image corresponding to yet another viewpoint different from that of FIG. 5A.

FIG. 5C illustrates an example of a 3D X-ray image 521 corresponding to yet another viewpoint different from that of FIG. 5A. Referring to FIG. 5C, the 3D X-ray image 521 is an image of a case where another viewpoint towards a part to be examined is changed when compared with the 3D X-ray image 501 of FIG. 5A. Since the viewpoint is changed, the viewpoint of the 3D X-ray image 521 is different from the viewpoint of the 3D X-ray image 501 of FIG. 5A.

Referring back to FIG. 1, the image acquisition apparatus 10 may acquire X-ray images at different rotation angles as described above. Thus, the 3D image processing unit 3211 may generate 3D X-ray images with respect to different directions of the part 2 to be examined. In other words, even in response to a viewpoint towards the part 2 to be examined being changed by a request of the user, a 3D X-ray image corresponding to the changed viewpoint may be generated and displayed.

Thus, because the user, such as an examiner, may perceive in various directions information regarding a position, size, and depth of a tumor even if the tumor is hidden by overlapped tissues inside a human body, accuracy of the examiner's diagnosis using X-ray images may increase, resulting in a better prescription and treatment.

Figure 6:
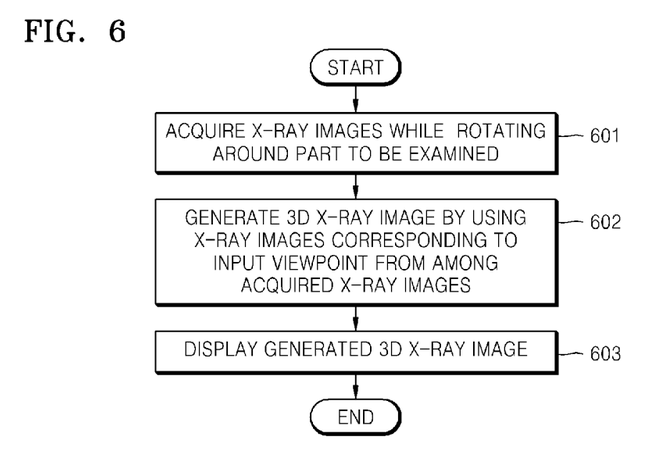
FIG. 6 is a flowchart illustrating an example of a method of providing a stereoscopic X-ray image.

FIG. 6 illustrates a method of providing a stereoscopic X-ray image. Referring to FIG. 6, the method of providing a stereoscopic X-ray image includes operations processed by the stereoscopic X-ray image providing system 1 shown in FIG. 1. Thus, although omitted below for conciseness, the content described in association with the stereoscopic X-ray image providing system 1 shown in FIG. 1 may also be applied to the method of providing a stereoscopic X-ray image.

In operation 601, the image acquisition apparatus 10 may acquire X-ray images captured at respective rotation angles with respect to the part 2 to be examined of a patient while rotating around the part 2 to be examined.

In operation 602, in response to information regarding a viewpoint with respect to the part 2 to be examined being input, the image generation apparatus 30 may generate a 3D X-ray image by using X-ray images of rotation angles corresponding to the viewpoint from among the acquired X-ray images.

In operation 603, the display apparatus 40 may display the generated 3D X-ray image.

Figure 7:
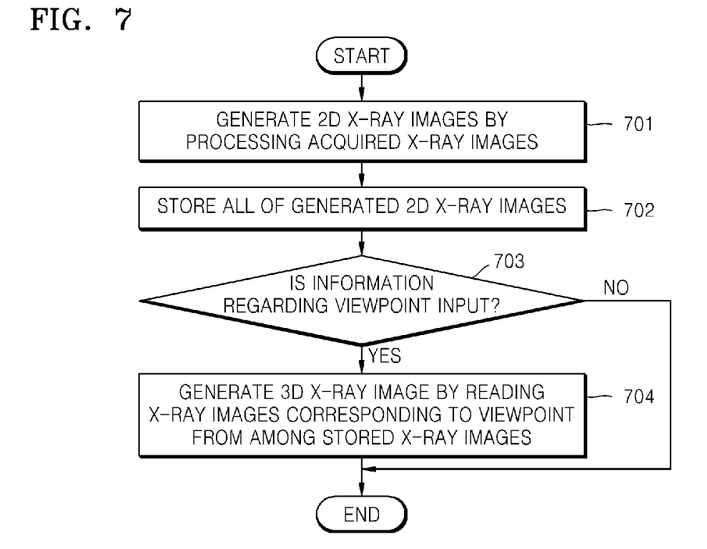
FIG. 7 is a flowchart illustrating an example of a method of generating a 3D X-ray image.

FIG. 7 illustrates a method of generating a 3D X-ray image. Referring to FIG. 7, the method of generating a 3D X-ray image includes operations processed by the image generation apparatus 30 shown in FIG. 3. Thus, although omitted below for conciseness, the content described in association with the image generation apparatus 30 shown in FIG. 3 may also be applied to the method of generating a 3D X-ray image.

In operation 701, the 2D image processing unit 3210 may process X-ray images acquired by the image acquisition apparatus 10 while the image acquisition apparatus 10 is rotating to generate 2D X-ray images.

In operation 702, the image storage unit 310 stores all of the generated 2D X-ray images. After the storage of the generated 2D X-ray images, the method proceeds to operation 703.

In operation 703, the input apparatus 20 connected to the image generation apparatus 30 determines whether information regarding a viewpoint desired by a user to view the part 2 to be examined is input by the user.

In operation 704, in response to the information regarding the viewpoint being input by the user, the 3D image processing unit 3211 reads X-ray images corresponding to the viewpoint from among stored X-ray images to generate a 3D X-ray image and processes the read X-ray images as the 3D X-ray image.

As described above, according to the one or more of the above examples of the description, by providing to an examiner, such as a doctor, a 3D X-ray image generated using X-ray images acquired at various angles with respect to a part of a patient, which is to be examined, the examiner may perceive information regarding a position, size, and depth of a tumor hidden by overlapped tissues inside a human body, so accuracy of the examiner's diagnosis using the 3D X-ray image may increase, resulting in a better prescription and treatment.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of providing a stereoscopic X-ray image, the method comprising:
    acquiring, at an image acquisition apparatus, two-dimensional (2D) X-ray images captured at respective rotation angles with respect to a part of a patient to be examined while rotating around the part to be examined;
    receiving, at an input apparatus, information regarding a viewpoint indicating a direction desired to view with respect to the part to be examined; and
    in response to the information regarding the viewpoint being received, generating, at an image generation apparatus, a three-dimensional (3D) X-ray image corresponding to the viewpoint by using 2D X-ray images at respective rotation angles corresponding to the viewpoint from among the acquired 2D X-ray images.

2. The method of claim 1, wherein the generating comprises, in response to the viewpoint being changed, using 2D X-ray images at rotation angles corresponding to the changed viewpoint to generate a 3D X-ray image.

3. The method of claim 1, wherein the generating includes generating the 3D X-ray image based on binocular disparity, and
the 2D X-ray images corresponding to the viewpoint are at least one pair of 2D X-ray images respectively corresponding to both eyes of a user from among the acquired 2D X-ray images.

4. The method of claim 1, wherein the 2D X-ray images captured at the respective rotation angles are captured under a same X-ray dose condition.

5. The method of claim 4, wherein the X-ray dose condition is changed via a user input.

6. The method of claim 1, wherein the generating comprises:
storing the acquired 2D X-ray images; and
in response to the information regarding the viewpoint being received by a user, reading 2D X-ray images corresponding to the viewpoint from among the stored 2D X-ray images and processing the read 2D X-ray images as a 3D X-ray image.

7. The method of claim 1, further comprising receiving the information regarding an X-ray dose condition with respect to the part to be examined.

8. The method of claim 1, wherein the acquiring includes acquiring the 2D X-ray images by using at least one X-ray generator.

9. The method of claim 8, wherein the acquiring includes, in response to two or more X-ray generators being used, using the X-ray generators to acquire at least one pair of 2D X-ray images at the same time.

10. A non-transitory computer-readable recording medium storing a computer-readable program for executing the method of claim 1 in a computer.

11. A system for providing a stereoscopic X-ray image, the system comprising:
an image acquisition apparatus configured to acquire two-dimensional (2D) X-ray images captured at respective rotation angles with respect to a part of a patient to be examined while rotating around the part to be examined;
an input apparatus configured to receive information regarding a viewpoint indicating a direction desired to view with respect to the part to be examined; and
an image generation apparatus configured to, in response to information regarding the viewpoint being received, generate a three-dimensional (3D) X-ray image corresponding to the viewpoint by using 2D X-ray images at respective rotation angles corresponding to the viewpoint from among the acquired 2D X-ray images.

12. The system of claim 11, wherein, in response to the viewpoint being changed, the image generation apparatus uses 2D X-ray images at rotation angles corresponding to the changed viewpoint to generate a 3D X-ray image.

13. The system of claim 11, wherein the image generation apparatus generates the 3D X-ray image based on binocular disparity, and
the 2D X-ray images corresponding to the viewpoint are at least one pair of 2D X-ray images respectively corresponding to both eyes of a user from among the acquired 2D X-ray images.

14. The system of claim 11, wherein the 2D X-ray images captured at the respective rotation angles are captured under a same X-ray dose condition.

15. The system of claim 14, wherein the X-ray dose condition is changed via a user input.

16. The system of claim 11, wherein the image generation apparatus comprises:
an image storage unit configured to store the acquired 2D X-ray images; and
a 3D image processing unit configured to, in response to the information regarding the viewpoint being received by a user, read 2D X-ray images corresponding to the viewpoint from among the stored 2D X-ray images and process the read 2D X-ray images as a 3D X-ray image.

17. The system of claim 11, wherein the input apparatus is configured to receive the information regarding an X-ray dose condition with respect to the part to be examined.

18. The system of claim 11, wherein the image acquisition apparatus using at least one X-ray generator to acquire the 2D X-ray images, and
in response to two or more X-ray generators being used, the image acquisition apparatus uses the X-ray generators to acquire at least one pair of 2D X-ray images at the same time.

19. The method of claim 1, further comprising displaying the generated 3D X-ray images.

* * * * *